United States Patent
Otsuki (10) Patent No.: US 10,233,813 B2
(45) Date of Patent: Mar. 19, 2019

(54) EXHAUST GAS MEASUREMENT SYSTEM

(71) Applicant: HORIBA, Ltd., Kyoto (JP)

(72) Inventor: Yoshinori Otsuki, Kyoto (JP)

(73) Assignee: HORIBA Ltd., Kyoto (JP)

( * ) Notice: Subject to any disclaimer, the term of this patent is extended or adjusted under 35 U.S.C. 154(b) by 90 days.

(21) Appl. No.: 15/099,141

(22) Filed: Apr. 14, 2016

(65) Prior Publication Data
US 2016/0312682 A1 Oct. 27, 2016

(30) Foreign Application Priority Data
Apr. 24, 2015 (JP) ................. 2015-089487

(51) Int. Cl.
| | |
|---|---|
| *F01N 11/00* | (2006.01) |
| *G01M 15/10* | (2006.01) |
| *F01N 13/08* | (2010.01) |
| *G01N 15/06* | (2006.01) |
| *G01N 33/00* | (2006.01) |

(52) U.S. Cl.
CPC ............ *F01N 11/002* (2013.01); *F01N 11/00* (2013.01); *F01N 13/08* (2013.01); *G01M 15/102* (2013.01); *G01N 15/0618* (2013.01); *G01N 33/0026* (2013.01); *F01N 2270/10* (2013.01); *F01N 2550/04* (2013.01); *F01N 2550/14* (2013.01); *F01N 2560/00* (2013.01); *Y02T 10/47* (2013.01)

(58) Field of Classification Search
CPC ........ F01N 11/00; F01N 11/002; F01N 13/08; F01N 2270/10; F01N 2550/04; F01N 2560/00; G01M 15/102; G01N 15/0618; G01N 33/0026
See application file for complete search history.

(56) References Cited

U.S. PATENT DOCUMENTS 4,633,706 A * 1/1987 Ito ................. G01M 15/106
73/23.33
5,138,163 A * 8/1992 Butler ............ G01N 21/3504
250/339.08

(Continued)

FOREIGN PATENT DOCUMENTS

| EP | 0630676 A1 | 12/1994 |
|---|---|---|
| EP | 2772744 A1 | 9/2014 |

(Continued)

OTHER PUBLICATIONS

EESR dated Sep. 8, 2016 issued for European Patent Application No. 16 165 686.3, 7 pgs.

*Primary Examiner* — Daniel S Larkin
(74) *Attorney, Agent, or Firm* — Brooks Kushman P.C.

(57) ABSTRACT

In order to surely remove deposits attached on the inner wall of an exhaust gas pipe, an exhaust gas measurement system that measures components contained in the exhaust gas of an internal combustion engine is adapted to include an exhaust gas piping member into which the exhaust gas is introduced; a purge gas supply mechanism adapted to supply purge gas to the exhaust gas piping member; a heating mechanism adapted to heat the exhaust gas piping member; and a control mechanism adapted to, after the heating mechanism has heated the exhaust gas piping member or the exhaust gas flowing through the exhaust gas piping member to a predetermined temperature, control the purge gas supply mechanism to start supplying the purge gas.

14 Claims, 6 Drawing Sheets

(56) References Cited

U.S. PATENT DOCUMENTS

| | | | | |
|---|---|---|---|---|
| 5,401,468 A * | 3/1995 | Patashnick | ......... | G01N 15/0618 |
| | | | | 422/78 |
| 5,456,124 A * | 10/1995 | Colvin | ...................... | G01F 1/48 |
| | | | | 73/114.71 |
| 5,531,105 A * | 7/1996 | Leong | ................. | G01M 15/102 |
| | | | | 73/114.52 |
| 5,821,435 A * | 10/1998 | Kojima | ................. | B01D 53/30 |
| | | | | 73/863.01 |
| 7,604,010 B2 * | 10/2009 | Hasebe | ............... | C23C 16/4405 |
| | | | | 134/1.1 |
| 9,341,545 B2 * | 5/2016 | Forster | .................... | F01N 11/00 |
| 2013/0118605 A1* | 5/2013 | Okada | .................. | F16L 53/001 |
| | | | | 137/334 |
| 2013/0312486 A1* | 11/2013 | Nakagawa | ........... | G01N 1/2252 |
| | | | | 73/23.31 |
| 2013/0312615 A1* | 11/2013 | Miyai | ................. | G01N 1/2247 |
| | | | | 96/400 |

FOREIGN PATENT DOCUMENTS

| | | |
|---|---|---|
| JP | 2000-221123 A | 8/2000 |
| JP | 2012-026892 A | 2/2012 |

\* cited by examiner

EXHAUST GAS MEASUREMENT SYSTEM

CROSS-REFERENCE TO RELATED APPLICATION

This application claims priority to JP Application No. 2015-089487, filed Apr. 24, 2015, the disclosure of which is incorporated in its entirety by reference herein.

TECHNICAL FIELD

The present invention relates to an exhaust gas measurement system adapted to measure components contained in the exhaust gas of an internal combustion engine.

DESCRIPTION OF THE RELATED ART

As a method for measuring the mass of particulate matter (hereinafter also referred to as PM) contained in exhaust gas, for example, as disclosed in JP-A2012-26892, there is known a so-called filter weighing method that collects PM by providing a filter in an exhaust gas pipe through which exhaust gas flows, and then weighs the mass of the collected PM.

When measuring exhaust gas components using some method such as the above-described filter weighing method, if there are deposits on the inner wall of the exhaust gas pipe, the deposits may peel off to cause a measurement error, and therefore it is adapted to remove the deposits before the measurement by flowing purge gas through the exhaust gas pipe.

When doing this, if substances such as gaseous components contained in the exhaust gas are condensed and attached on the inner wall, such deposits are difficult to remove only by flowing the purge gas, and therefore it is adapted to peel and remove the condensed substances such as the condensed gaseous components from the inner wall by heating the exhaust gas pipe while flowing the purge gas.

However, since this method heats the exhaust gas pipe while supplying the purge gas, it is impossible to sufficiently raise the temperature of the exhaust gas pipe, and surely remove the deposits.

In addition, apart from the above-described method, there is a possible method that heats the purge gas to high temperature and then flows the purge gas through the exhaust gas pipe. However, this method separately requires equipment for heating the purge gas, and consequently the system becomes large-scale as a whole.

SUMMARY OF INVENTION

Technical Problem

Therefore, the present invention is made in order to solve the above-described problems, and a main object thereof is to surely remove deposits attached on the inner wall of an exhaust gas pipe.

Solution to Problem

That is, an exhaust gas measurement system according to the present invention is one that measures a component contained in exhaust gas of an internal combustion engine, and includes: an exhaust gas piping member into which the exhaust gas is introduced; a purge gas supply mechanism adapted to supply purge gas to the exhaust gas piping member; a heating mechanism adapted to heat the exhaust gas piping member; and a control mechanism adapted to, after the heating mechanism has heated the exhaust gas piping member or the exhaust gas flowing through the exhaust gas piping member to a predetermined temperature, control the purge gas supply mechanism to start supplying the purge gas.

The exhaust gas measurement system as described above heats the exhaust gas piping member or the exhaust gas flowing through the exhaust gas piping member to the predetermined temperature to bring deposits attached on the inner wall of the exhaust gas piping member into a peelable state, and then makes the control mechanism start supplying the purge gas, and can therefore surely remove the deposits.

Also, it is not necessary to separately provide equipment for heating the purge gas, and therefore it is also not necessary to make the system large-scale as a whole.

Preferably, before the control mechanism finishes supplying the purge gas, the heating mechanism finishes heating the exhaust gas piping member.

Such a configuration makes it possible to sufficiently cool the exhaust gas piping member using the purge gas, and therefore safely make the exhaust gas component measurement, preparation for the measurement, and the like after the purge.

Preferably, the exhaust gas measurement system further includes a temperature sensor provided in the exhaust gas piping member, and the control mechanism is configured to obtain a temperature detection signal from the temperature sensor, and also after a value indicated by the temperature detection signal has reached the predetermined temperature, start supplying the purge gas.

Such a configuration makes it possible to, after surely heating the exhaust gas piping member or the exhaust gas flowing through the exhaust gas piping member to the predetermined temperature, supply the purge gas, and therefore more surely remove the deposits.

Configurations adapted to eliminate the need for the above-described temperature sensor to simplify the system include one in which after a predetermined time has passed since the heating mechanism started heating the exhaust gas piping member, the control mechanism starts supplying the purge gas.

Preferably, the exhaust gas piping member is provided with a filter adapted to collect particulate matter in the exhaust gas.

In such a configuration, since deposits peeled from the inner wall are collected by the filter, by measuring the amount of the collected deposits, the degree of soiling inside the exhaust gas piping member can be compared with, for example, the degree of soiling at the normal time, and thereby it can be known whether or not a test was normally done.

A specific embodiment may be such that the exhaust gas measurement system is configured to further include a diluent gas piping member that is connected to the exhaust gas piping member and adapted to conduct diluent gas for diluting the exhaust gas to the exhaust gas piping member, in which the purge gas supply mechanism flows the purge gas to the diluent gas piping member to supply the purge gas to the exhaust gas piping member.

In such a configuration, it is not necessary to take the trouble to provide a dedicated piping member for supplying the purge gas to the exhaust gas piping member, and the purge gas can be supplied to the exhaust gas piping member using the existing piping member.

If the purge gas is the diluent gas, the diluent gas can also be used as the purge gas.

Also, an exhaust gas measuring method according to the present invention is a method that measures a component contained in exhaust gas of an internal combustion engine, and after heating an exhaust gas piping member into which the exhaust gas is introduced or the exhaust gas flowing through the exhaust gas piping member to a predetermined temperature, starts supplying purge gas to the exhaust gas piping member.

Such a method can produce the same working effect as that of the above-described exhaust gas measurement system.

Advantageous Effects of Invention

According to the present invention configured as described above, without making the system large-scale as a whole, the deposits on the inner wall of the exhaust gas piping member can be surely removed, and thereby the exhaust gas component can be accurately measured.

DESCRIPTION OF EMBODIMENTS

One embodiment of the exhaust gas measurement system according to the present invention will be described below.

An exhaust gas measurement system 100 of the present embodiment is one adapted to measure particulate matter (hereinafter also referred to as PM) contained in the exhaust gas of an unillustrated internal combustion engine, and here configured to collect and dilute part of the exhaust gas discharged from the internal combustion engine, and then conduct the total amount of the collected and diluted exhaust gas to an exhaust gas component measuring device 30.

Figure 1:
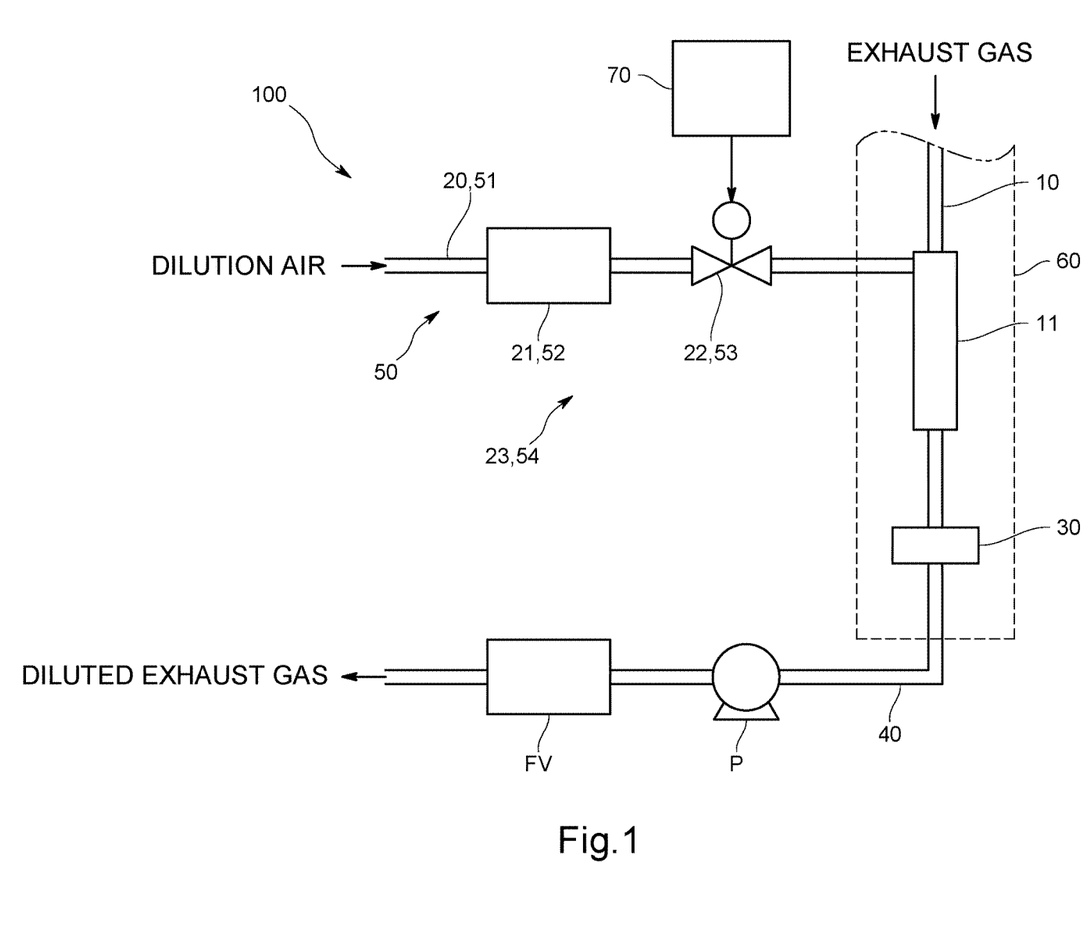
FIG. 1 is a diagram schematically illustrating the configuration of an exhaust gas measurement system of the present embodiment.

Specifically, as illustrated in FIG. 1, the exhaust gas measurement system 100 is one including: an exhaust gas piping member 10 (hereinafter simply referred to as an exhaust gas pipe 10) into which the exhaust gas of the internal combustion engine is introduced; a diluent gas piping member 20 (hereinafter simply referred to as an diluent gas pipe 20) through which diluent gas for diluting the exhaust gas is supplied to the exhaust gas pipe 10, and the exhaust gas component measuring device 30 adapted to measure the exhaust gas conducted through the exhaust gas pipe 10.

The exhaust gas pipe 10 of which one end is provided, for example, inside an unillustrated exhaust pipe of the internal combustion engine and the other end is connected to the exhaust gas composition measuring device 30 is one that collects the part of the exhaust gas discharged from the internal combustion engine in a flow separation manner and conducts the collected exhaust gas to the exhaust gas measuring device 30.

Specifically, the exhaust gas pipe 10 has a dilution tunnel 11 such as a micro tunnel, and the dilution tunnel 11 is connected with the above-described diluent gas pipe 20. This configuration allows the part of the exhaust gas discharged from the internal combustion engine to be diluted in the dilution tunnel 11 and then flow into the exhaust gas component measuring device 30.

Note that the exhaust gas pipe 10 may be one having a so-called full tunnel adapted to introduce the total amount of the exhaust gas discharged from the internal combustion engine into the dilution tunnel 11.

The diluent gas pipe 20 is one that conducts the diluent gas to the dilution tunnel 11, of which one end is connected to an unillustrated diluent gas source and the other end is connected to the dilution tunnel 11.

The diluent gas pipe 20 in the present embodiment is provided with a diluent gas flow rate control part 23 having a flowmeter 21 such as a venturi, a flow rate control valve 22, and the like, and adapted to be able to control the flow rate of the diluent gas to be supplied to the exhaust gas pipe 10.

In addition, in the present embodiment, the diluent gas is air.

The exhaust gas component measuring device 30 is one that is provided on the downstream side of the dilution tunnel 11 and measures various components contained in the diluted exhaust gas, and here a collection filter adapted to collect the PM contained in the exhaust gas.

The collection filter is connected with an exhaust pipe 40 through which the exhaust gas having passed through the collection filter flows, and the exhaust pipe 40 is provided with: a suction pump P (e.g., a roots blower) of which suction capability can be varied by controlling a rotation speed; and a flowmeter FV provided downstream of the suction pump P, such as a venturi.

In addition, in the present embodiment, the exhaust gas having passed through the collection filter flows through the exhaust pipe 40 and is discharged outside.

As illustrated in FIG. 1, the exhaust gas measurement system 100 according to the present invention is adapted to further include: a purge gas supply mechanism 50 adapted to supply purge gas to the exhaust gas pipe 10; a heating mechanism 60 adapted to heat the exhaust gas pipe 10; and a control mechanism 70 adapted to control the purge gas supply mechanism 50.

The purge gas supply mechanism 50 includes: an unillustrated purge gas source; a purge gas piping member 51 (hereinafter simply referred to as a purge gas pipe 51) of which one end is connected to the purge gas source and the other end is connected to the exhaust gas pipe 10; and a purge gas flow rate control part 54 that is provided in the purge gas pipe 51 and has a flowmeter 52 such as a venturi, a flow rate control valve 53, and the like.

The purge gas supply mechanism 50 here is one adapted to supply the above-described diluent gas, i.e., air to the exhaust gas pipe 10 as the purge gas, in which the purge gas source is the above-described diluent gas source, and the purge gas pipe 51 is the above-described diluent gas pipe 20. In other words, the diluent gas source and the diluent gas pipe 20 in the present embodiment are also used as the purge gas source and the purge gas pipe 51, respectively. In addition, the flowmeter 21 and the flow rate control valve 22 constituting the diluent gas flow rate control part 23 here are also used as the flowmeter 52 and the flow rate control valve 53 of the purge gas flow rate control part 54, respectively.

The heating mechanism 60 is one adapted to heat the inner wall of the exhaust gas pipe 10 or heat the exhaust gas flowing through the exhaust gas pipe 10, and configured to heat a part or whole of the exhaust gas pipe 10.

The heating mechanism 60 in the present embodiment is one that heats the exhaust gas pipe 10 from the one end part to the other end part, i.e., the whole of the exhaust gas pipe 10 using, for example, a heater or the like, and here switches between heating and a stop by obtaining an externally inputted ON/OFF signal.

Further, the control mechanism 70 controls the purge gas supply mechanism 50 to start supplying the purge gas after the heating mechanism 60 have heated the exhaust gas pipe 10 to a predetermined temperature.

Figure 2:
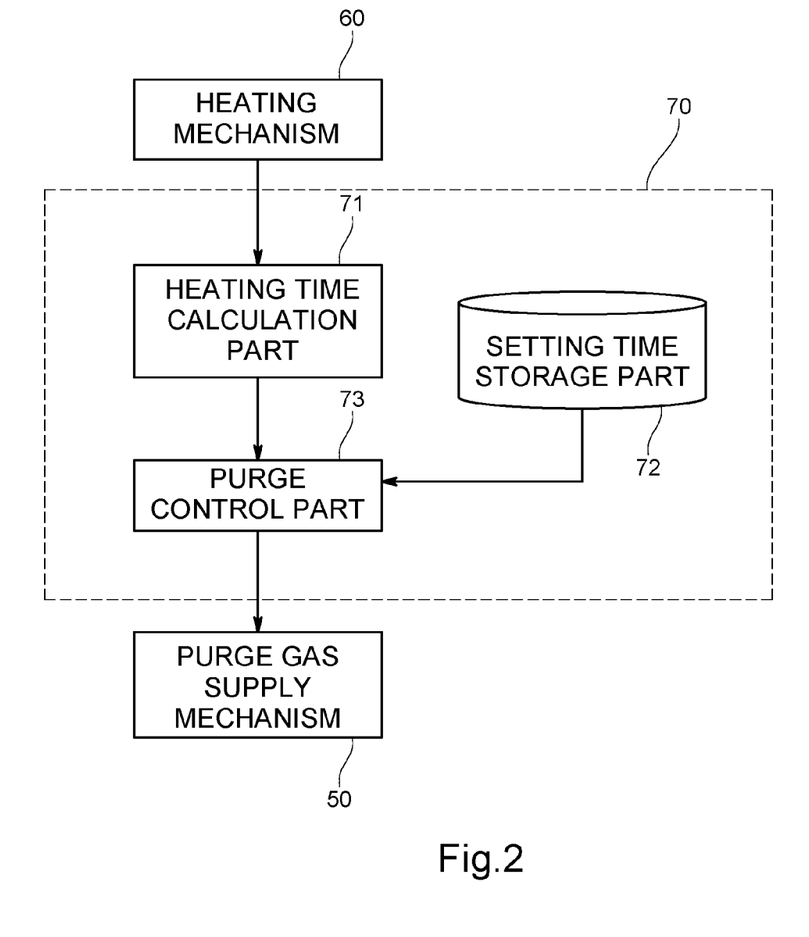
FIG. 2 is a functional block diagram illustrating functions of a control mechanism in the same embodiment.

Specifically, the control mechanism 70 is one including some components such as a CPU, a memory, an A/D converter, and a D/A converter. In addition, as illustrated in FIG. 2, the control mechanism 70 is configured to function as a heating time calculation part 71, a setting time storage part 72, and a purge control part 73 by making the CPU and peripheral devices cooperate in accordance with a program stored in a predetermined area of the memory.

In the following, the actions of the control mechanism 70 will be described while describing the respective parts.

The heating time calculation part 71 is one that obtains the above-described ON/OFF signal inputted to the heating mechanism 60 as well as on the basis of the ON/OFF signal, calculating a heating time during which the heating mechanism 60 keeps heating the exhaust gas pipe 10.

The setting time storage part 72 is formed in a predetermined area of the memory, and as a setting time, preliminarily stores a time equal to or more than the time from when the heating mechanism 60 starts heating the exhaust gas pipe 10 to when the temperature of the exhaust gas pipe 10 reaches the predetermined temperature (hereinafter also referred to as a preparation temperature). In the present embodiment, a time equal to or more than the time required for the temperature of the inner wall of the exhaust gas pipe 10 to reach the preparation temperature is stored as the setting time.

Note that the term "preparation temperature" here refers to a temperature at which volatile components having high boiling points come out, such as the gaseous components condensed and attached on the inner wall of the exhaust gas pipe 10, and is specifically approximately 200° C. Also, the setting time can be appropriately changed by some means such as the settings of the heating mechanism 60, but is here approximately 1 to 2 hours.

The purge control part 73 is one that starts supplying the purge gas after a predetermined time has passed since the heating mechanism 60 started heating the exhaust gas pipe 10.

Figure 3:
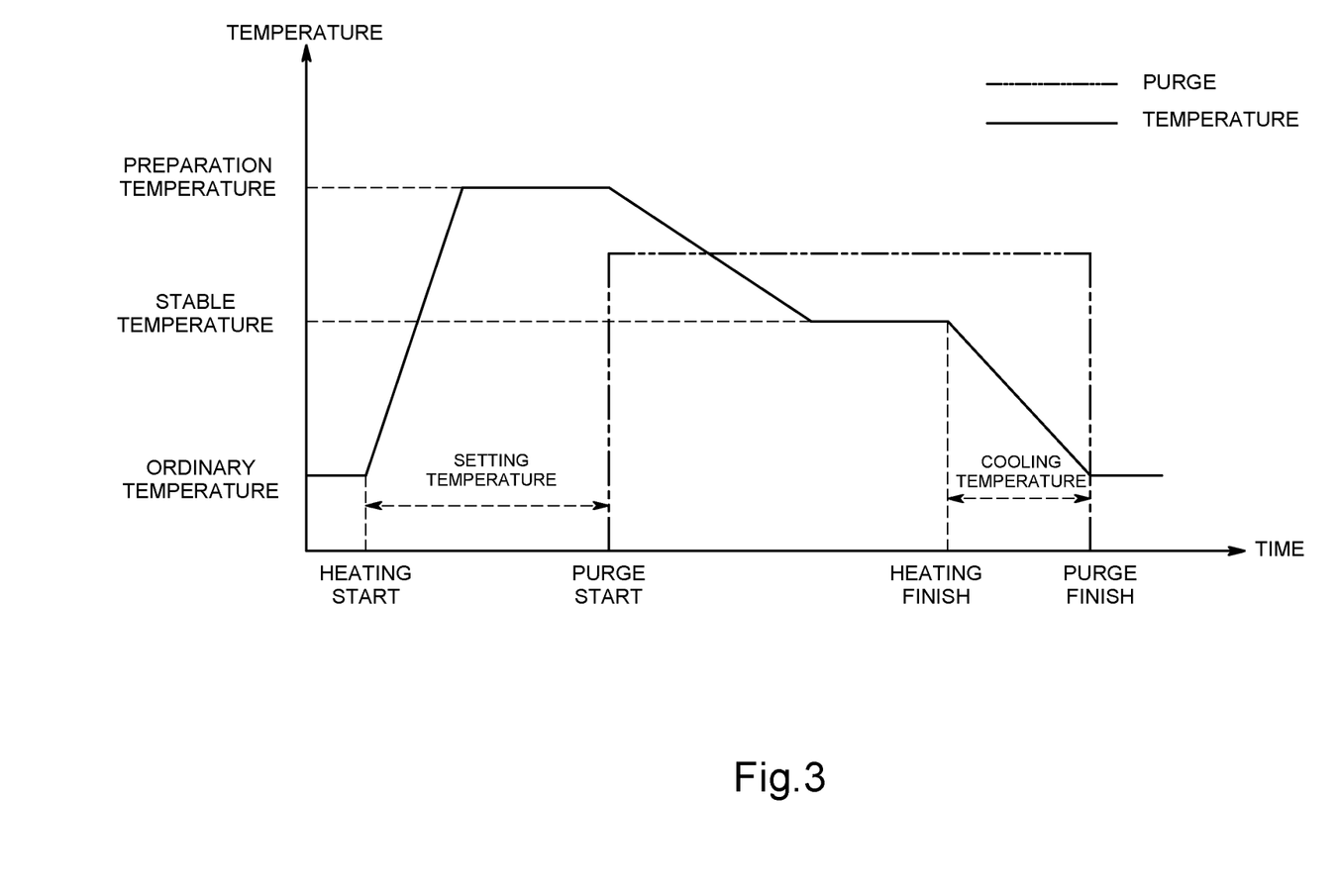
FIG. 3 is a graph for explaining the actions of the control mechanism in the same embodiment.

The purge control part 73 in the present embodiment is configured to obtain the heating time and the setting time as well as, as illustrated in FIG. 3, when the heating time reaches the setting time, transmitting a control signal to the purge gas supply mechanism 50 to start supplying the purge gas.

Specifically, the purge control part 73 transmits the control signal to the purge gas flow rate control part 54 provided in the purge gas pipe 51, and thereby brings the flow rate control valve 53 into an open state.

When doing this, in order to purge the whole of the exhaust gas pipe 10, it is adapted to stop the suction pump P provided in the exhaust pipe 40 and allow the purge gas to reach both of the upstream and downstream sides of the exhaust gas pipe 10 through the purge gas pipe 51.

In addition, when the supply of the purge gas is started, as illustrated in FIG. 3, the exhaust gas pipe 10 is cooled by the purge gas to decrease the temperature of the exhaust gas pipe 10 from the preparation temperature to a stable temperature.

After that, the purge gas control part 73 may be adapted to, as illustrated in FIG. 3, finish supplying the purge gas after a predetermined time (hereinafter also referred to as a cooling time) has passed since the above-described heating mechanism 60 finished heating the exhaust gas pipe 10. In other words, the heating mechanism 60 may be adapted to finish heating the exhaust gas pipe 10 before the purge control part 73 finishes supplying the purge gas.

Specifically, the purge control part 73 obtains the ON/OFF signal inputted to the heating mechanism 60 as well as after the cooling time has passed since the ON/OFF signal was switched from ON to OFF, transmitting the control signal to the purge gas flow rate control part 54 to bring the flow rate control valve 53 into a close state.

That is, the purge control part 73 in the present embodiment is configured to keep supplying the purge gas to the exhaust gas pipe 10 until the cooling time passes after the heating mechanism 60 has finished the heating.

In doing so, the exhaust gas pipe 10 or the exhaust gas flowing through the exhaust gas pipe 10 is cooled from the stable temperature to ordinary temperature.

The exhaust gas measurement system 100 according to the present embodiment configured as described heats the exhaust gas pipe 10 or the exhaust gas flowing through the exhaust gas pipe 10 to the preparation temperature to bring the gaseous components condensed and attached on the inner surface of the exhaust gas pipe 10 into a state of coming out, and then makes the purge control part 73 start supplying the purge gas, and can therefore surely remove the deposits on the inner wall.

Also, it is not necessary to separately provide equipment for heating the purge gas, and therefore the deposits can be removed without making the system large-scale as a whole.

In addition, since the purge control part 73 starts supplying the purge gas after the predetermined time has passed since the heating mechanism 60 started heating the exhaust gas pipe 10, the exhaust gas pipe 10 is not cooled by the purge gas during the heating, and therefore the exhaust gas pipe 10 can be made to reach the predetermined temperature faster. Also, the temperature of the exhaust gas pipe 10 can be made higher even with the same quantity of heat supplied, thus making it possible to save energy.

Further, since the purge control part 73 keeps supplying the purge gas to the exhaust gas pipe 10 until the cooling time passes after the heating mechanism 60 has finished the heating, the exhaust gas pipe 10 can be cooled to the ordinary temperature by the purge gas, and therefore the exhaust gas measurement, preparation for the measurement, and the like after the purge can be safely made.

In addition, since the exhaust gas pipe 10 is provided with the collection filter as the exhaust gas component measuring device 30, the deposits removed from the inner wall of the exhaust gas pipe 10 by the purge are collected by the collection filter. After that, by measuring the amount of the collected deposits, the degree of soiling inside the exhaust gas pipe 10 can be compared with, for example, the degree of soiling at the normal time, and thereby it can be known whether or not a test done before the purge was normal.

In addition, since the diluent gas source and the diluent gas pipe 20 are also used as the purge gas source and the purge gas pipe 51, respectively, it is not necessary to take the trouble to provide a dedicated gas source and pipe for supplying the purge gas to the exhaust gas pipe 10, and the purge gas can be supplied to the exhaust gas pipe 10 using the existing gas source and pipe.

Note that the present invention is not limited to the above-described embodiment.

For example, the above-described embodiment is adapted to make the purge control part start supplying the purge gas after the predetermined time has passed since the heating mechanism started heating the exhaust gas pipe, but may be adapted to provide a temperature sensor in the exhaust gas pipe and after a temperature detected by the temperature sensor has reached the predetermined preparation temperature, make the purge control part start supplying the purge gas.

Figure 4:
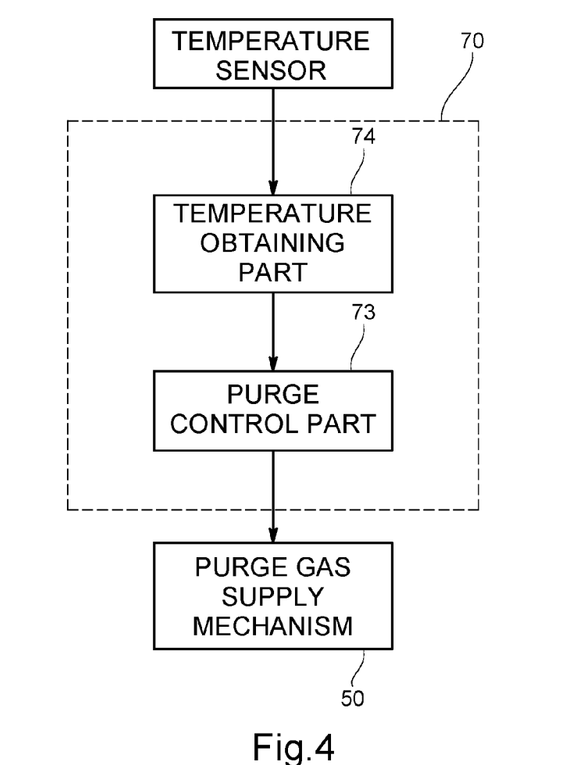
FIG. 4 is a functional block diagram illustrating functions of a control mechanism in a variation.

In this case, a specific configuration may be such that, as illustrated in FIG. 4, the control mechanism has a temperature obtaining part 74 adapted to obtain a temperature detection signal from the temperature sensor, and the purge control part 73 starts supplying the purge gas after a temperature indicated by the temperature detection signal obtained by the temperature obtaining part 74 has reached the preparation temperature.

Such a configuration makes it possible to start supplying the purge gas after the exhaust gas pipe or the exhaust gas flowing through the exhaust gas pipe has been surely heated to the preparation temperature, and therefore the deposits attached on the inner wall of the exhaust gas pipe can be surely removed.

Also, the control mechanism in the above-described embodiment is adapted to control the supply of the purge gas using the temperature of the exhaust gas pipe, but may be adapted to control the supply of the purge gas using the temperature of the exhaust gas flowing through the exhaust gas pipe.

Further, it may be adapted to provide the exhaust gas pipe with a concentration sensor adapted to detect the concentration of a predetermined component, and after the concentration detected by the concentration sensor has reached a predetermined concentration or more, make the purge control part start supplying the purge gas.

Figure 5:
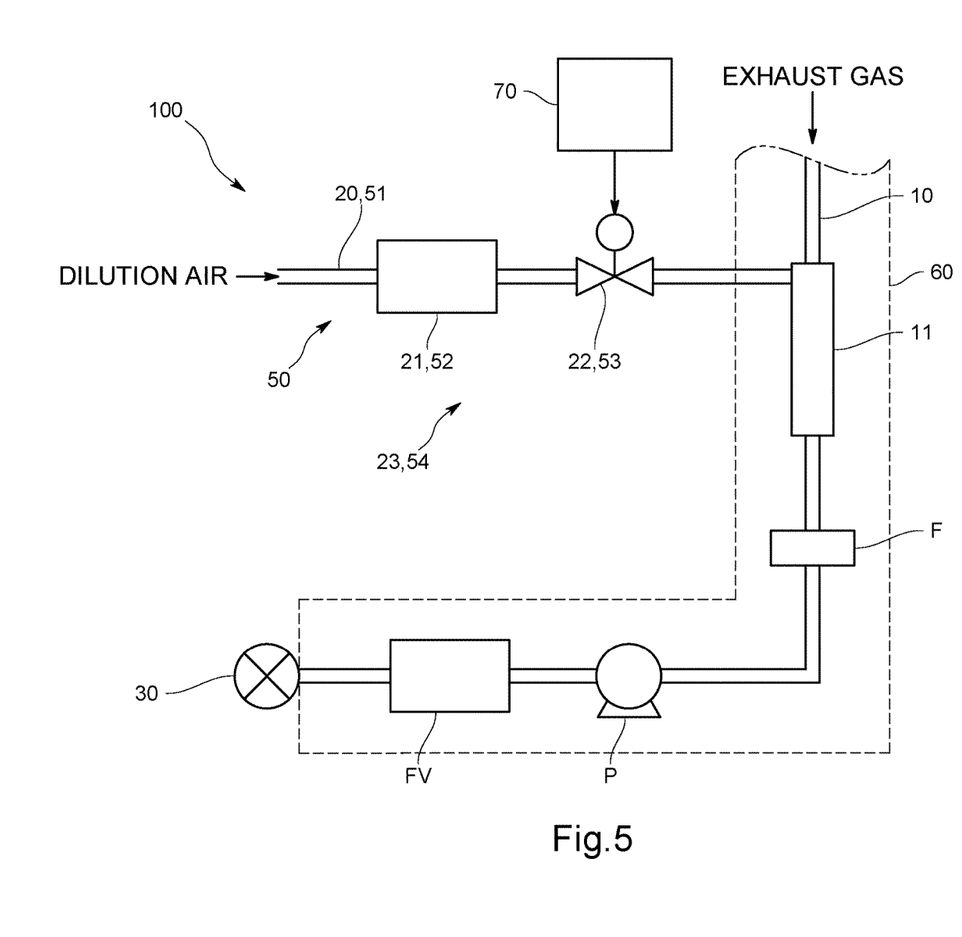
FIG. 5 is a diagram schematically illustrating the configuration of an exhaust gas measurement system of another variation.

Still further, the exhaust gas component measuring device in the above-described embodiment is the collection filter. However, as illustrated in FIG. 5, the exhaust gas component measuring device 30 may be one that is provided downstream of the collection filter F separately from the collection filter F, and specifically, as the exhaust gas component measuring device 30, a device such as a continuous PM meter adapted to continuously measure the PM in the exhaust gas or a THC meter adapted to measure hydrocarbons in the exhaust gas can be cited.

In this case, the other end of the exhaust gas pipe 10 is connected to the exhaust gas component measuring device 30 such as the continuous PM meter or the THC meter, and the exhaust gas pipe 10 is heated by the heating mechanism 60. That is, the exhaust gas measurement system 100 in this configuration does not have the exhaust pipe in the above-described embodiment.

Further, in the above-described embodiment, the diluent gas source and the diluent gas pipe are also used as the purge gas source and the purge gas pipe, respectively. However, the purge gas source and the purge gas pipe may be provided separately from the diluent gas source and the diluent gas pipe, respectively.

Figure 6:
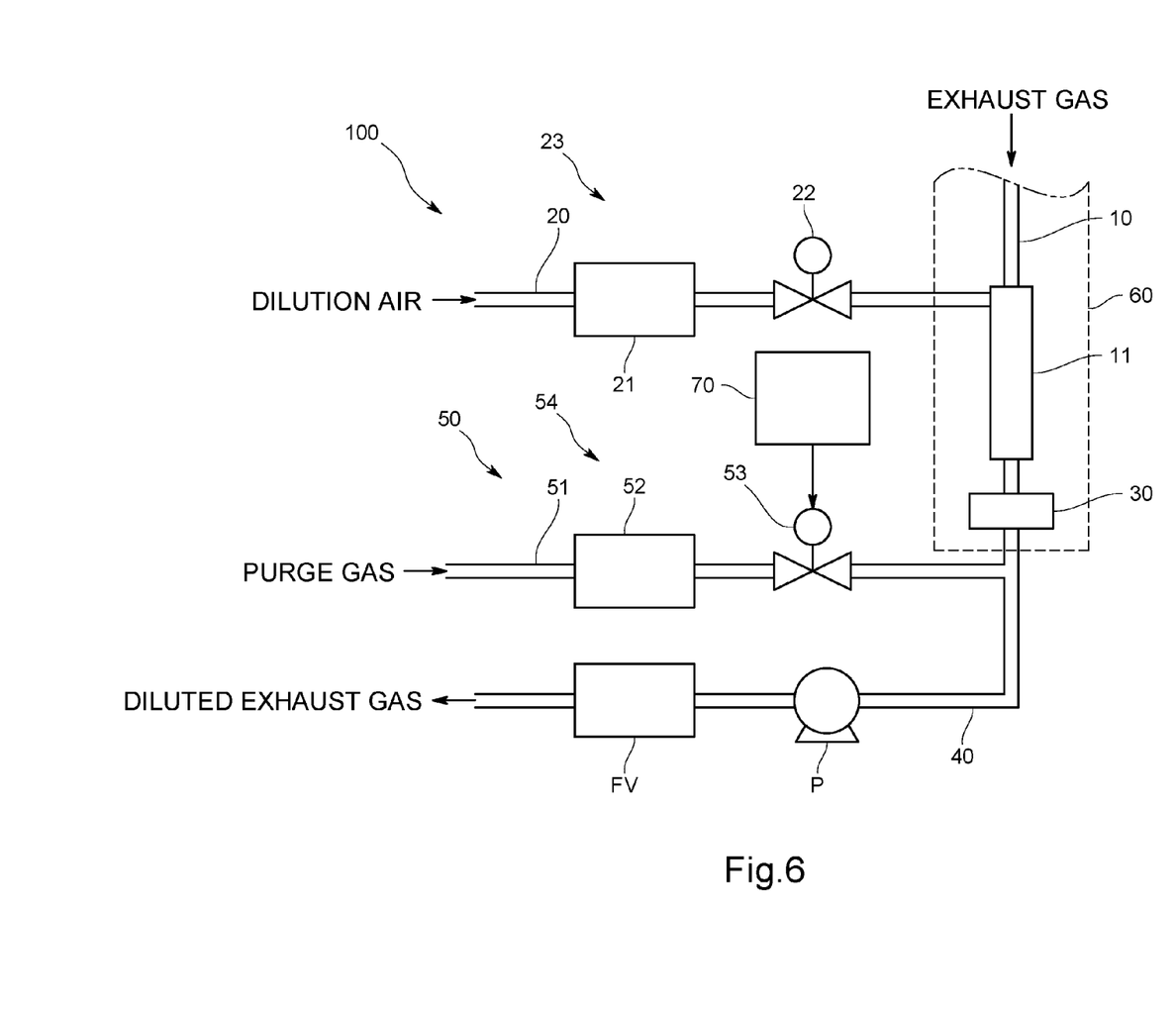
FIG. 6 is a diagram schematically illustrating the configuration of an exhaust gas measurement system of still another variation.

In this case, the purge gas pipe 51 is only required to be connected to the exhaust pipe 10, and specific configurations include one such as a configuration in which, as illustrated in FIG. 6, the purge gas pipe 51 is connected on the downstream side of the collection filter as the exhaust gas component measuring device 30.

In addition, the exhaust gas pipe in the above-described embodiment has the one dilution tunnel, but may be configured to have multiple dilution tunnels to dilute the exhaust gas discharged from the internal combustion engine in a multistep manner.

Note that in the case of using such a multistep dilution configuration, the temperature of the exhaust gas is relatively high on an upper step side and decreases toward a lower step side, and therefore in order to save energy and achieve high efficiency, the heating mechanism is preferably configured to heat an exhaust gas pipe in a lower step to higher temperature than the temperature of an exhaust gas pipe in a higher step.

Also, the heating mechanism is not necessarily required to heat the collecting filter, but may be adapted to heat only the exhaust gas pipe. In addition, the heating mechanism may be adapted to heat the purge gas pipe together with the exhaust gas pipe.

In addition, in the case where a material susceptible to heat is used for the collection filter, such as resin, it is impossible to heat the collection filter to high temperature, and therefore it is preferable to provide the heating mechanism with multiple heaters and, for example, make temperature after the outlet of the dilution tunnel in the exhaust gas pipe lower (e.g., 50° C.) than temperature before the outlet (e.g., 200° C.).

Further, the heating mechanism in the above-described embodiment is one that obtains the externally inputted ON/OFF signal. However, the control mechanism may be adapted to transmit an ON/OFF signal to the heating mechanism. That is, the control mechanism may be configured to control the heating mechanism together with the purge gas supply mechanism.

In addition, in the above-described embodiment, the time equal to or more than the time required for the temperature of the exhaust gas pipe or the temperature of the exhaust gas flowing through the exhaust gas pipe to reach the preparation temperature is defined as the setting time, but the time to reach the preparation temperature may be defined as the setting time. That is, it may be adapted to start supplying the purge gas simultaneously with when the temperature of the exhaust gas pipe or the temperature of the exhaust gas flowing through the exhaust gas pipe reaches the preparation time.

Also, it is not necessarily required to provide the cooling time in the above-described embodiment. That is, it may be adapted to finish supplying the purge gas simultaneously with when the heating mechanism finishes the heating.

In addition, the control mechanism may be configured to control the flow rate control valve provided in the diluent gas pipe and the suction pump provided in the exhaust pipe so as to make a flow rate through the diluent gas pipe and a flow rate through the exhaust pipe equal to each other.

In such a configuration, since the flow rate through the diluent gas pipe and the flow rate through the exhaust pipe can be made equal to each other, even while the internal combustion engine runs, the exhaust gas from the internal combustion engine does not theoretically flows into the exhaust gas pipe. In doing so, even in the case of making other exhaust gas analyses while running the internal combustion engine, the exhaust gas pipe can be purged without affecting these exhaust gas analyses.

In further addition, the exhaust gas measurement system may be configured to include an on/off valve provided on the upstream side of the dilution tunnel in the exhaust gas pipe, and in a state where the on/off valve is closed, make the heating mechanism heat the exhaust gas pipe as well as activating the suction pump provided in the exhaust pipe.

In doing so, since the exhaust gas pipe is heated while being evacuated, the deposits attached on the inner surface of the exhaust gas pipe can be made more peelable.

Note that after the end of the evacuation and heating, it is preferable to flow the purge gas through the exhaust gas pipe in order to discharge the peeled deposits.

In the above-described embodiment, the piping members are described as the pipes, respectively. However, a piping member may be, for example, a block body (a so-called manifold block) inside which a flow path is provided.

In this case, by connecting multiple block bodies consecutively, a flow path through which the exhaust gas or the like flows can be formed.

Also, the above-described embodiment is adapted such that the control mechanism determines the timing to start or finish supplying the purge gas, but may be adapted such that, for example, an operator starts or finishes supplying the purge gas while checking a temperature sensor attached to the exhaust gas pipe.

Besides, it goes without saying that the present invention is not limited to any of the above-described embodiment and variations, but can be variously modified without departing from the scope thereof.

REFERENCE SIGNS LIST

100: Exhaust gas measurement system
10: Exhaust gas pipe
11: Dilution tunnel
20: Diluent gas pipe
30: Exhaust gas component measuring device
50: Purge gas supply mechanism
51: Purge gas pipe
60: Heating mechanism
70: Control mechanism

What is claimed is:

1. An exhaust gas measurement system including an exhaust gas component measuring device that measures a component contained in exhaust gas of an internal combustion engine, the exhaust gas measuring system comprising:
   an exhaust gas piping member into which the exhaust gas is introduced;
   a purge gas supply arrangement, including a valve, adapted to supply purge gas to the exhaust gas piping member;
   one or more heaters adapted to heat the exhaust gas piping member; and
   a computer adapted to,
      other than during measuring of the exhaust gas component and after the one or more heaters has heated the exhaust gas piping member or the exhaust gas flowing through the exhaust gas piping member to a predetermined temperature, control the purge gas supply arrangement to start supplying the purge gas to peel and remove condensed gaseous components from inner walls of the exhaust gas piping member; and
      before the purge gas supply arrangement finishes supplying the purge gas, control the one or more heaters to finish heating the exhaust gas piping member.

2. The exhaust gas measurement system according to claim 1, further comprising
   a temperature sensor provided in the exhaust gas piping member, wherein
   the computer is further adapted to obtain a temperature detection signal from the temperature sensor, and after a value indicated by the temperature detection signal has reached the predetermined temperature, to control the purge gas supply arrangement to start supplying the purge gas.

3. The exhaust gas measurement system according to claim 1, wherein the computer is further adapted to, after a predetermined time has passed since the one or more heaters started heating the exhaust gas piping member, control the purge gas supply arrangement to start supplying the purge gas.

4. The exhaust gas measurement system according to claim 1, wherein
   the exhaust gas piping member is provided with a filter adapted to collect particulate matter in the exhaust gas.

5. The exhaust gas measurement system according to claim 1, further comprising
   a diluent gas piping member that is connected to the exhaust gas piping member and adapted to conduct diluent gas for diluting the exhaust gas to the exhaust gas piping member, wherein
   the purge gas supply arrangement is further adapted to flow the purge gas to the diluent gas piping member to supply the purge gas to the exhaust gas piping member.

6. The exhaust gas measurement system according to claim 5, wherein
   the purge gas is the diluent gas.

7. An exhaust gas measurement system including an exhaust gas component measuring device that measures a component contained in exhaust gas of an internal combustion engine, the exhaust gas measuring system comprising:
   an exhaust gas piping member into which the exhaust gas is introduced;
   a purge gas supply arrangement, including a valve, adapted to supply purge gas to the exhaust gas piping member;
   one or more heaters adapted to heat the exhaust gas piping member; and
   a computer adapted to,
      after the one or more heaters has heated the exhaust gas piping member or the exhaust gas flowing through the exhaust gas piping member to a predetermined temperature, control the purge gas supply arrangement to start supplying the purge gas, and
      before the purge gas supply arrangement finishes supplying the purge gas, control the one or more heaters to finish heating the exhaust gas piping member.

8. The exhaust gas measurement system according to claim 7, further comprising
   a temperature sensor provided in the exhaust gas piping member, wherein
   the computer is further configured to obtain a temperature detection signal from the temperature sensor, and after a value indicated by the temperature detection signal has reached the predetermined temperature, to control the purge gas supply arrangement to start supplying the purge gas.

9. The exhaust gas measurement system according to claim 7, wherein the computer is further configured to, after a predetermined time has passed since the one or more heaters started heating the exhaust gas piping member, control the purge gas supply arrangement to start supplying the purge gas.

10. The exhaust gas measurement system according to claim 7, wherein
the exhaust gas piping member is provided with a filter adapted to collect particulate matter in the exhaust gas.

11. The exhaust gas measurement system according to claim 7, further comprising
a diluent gas piping member that is connected to the exhaust gas piping member and adapted to conduct diluent gas for diluting the exhaust gas to the exhaust gas piping member, wherein
the purge gas supply arrangement is further adapted to flow the purge gas to the diluent gas piping member to supply the purge gas to the exhaust gas piping member.

12. The exhaust gas measurement system according to claim 11, wherein
the purge gas is the diluent gas.

13. An exhaust gas measurement system including an exhaust gas component measuring device that measures a component contained in exhaust gas of an internal combustion engine, the exhaust gas measuring system comprising:
an exhaust gas piping member into which the exhaust gas is introduced;
a diluent gas piping member that is connected to the exhaust gas piping member and adapted to conduct diluent gas for diluting the exhaust gas to the exhaust gas piping member;
a purge gas supply arrangement, including a valve, adapted to flow purge gas to the diluent gas piping member to supply the purge gas to the exhaust gas piping member;
one or more heaters adapted to heat the exhaust gas piping member; and
a computer adapted to, after the one or more heaters has heated the exhaust gas piping member or the exhaust gas flowing through the exhaust gas piping member to a predetermined temperature, control the purge gas supply arrangement to start supplying the purge gas.

14. A method for measuring a component contained in exhaust gas of an internal combustion engine with an exhaust gas component measuring device that includes an exhaust gas piping member into which the exhaust gas is introduced, a purge gas supply arrangement, including a valve, adapted to supply purge gas to the exhaust gas piping member, and one or more heaters adapted to heat the exhaust gas piping member, the method comprising:
after the one or more heaters has heated the exhaust gas piping member or the exhaust gas flowing through the exhaust gas piping member to a predetermined temperature, controlling the purge gas supply arrangement to start supplying the purge gas, and
before the purge gas supply arrangement finishes supplying the purge gas, controlling the one or more heaters to finish heating the exhaust gas piping member.

* * * * *